(12) United States Patent
Tong et al.

(10) Patent No.: US 8,303,830 B2
(45) Date of Patent: Nov. 6, 2012

(54) MICRO AND NANO SCALE SURFACE TEXTURED TITANIUM-CONTAINING ARTICLES AND METHODS OF PRODUCING SAME

(75) Inventors: Weidong Tong, Warsaw, IN (US); Lawrence Salvati, Goshen, IN (US); Stephanie A. Vass, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 135 days.

(21) Appl. No.: 12/754,290

(22) Filed: Apr. 5, 2010

(65) Prior Publication Data
US 2010/0268347 A1 Oct. 21, 2010

Related U.S. Application Data

(60) Provisional application No. 61/169,443, filed on Apr. 15, 2009.

(51) Int. Cl.
*B44C 1/22* (2006.01)
(52) U.S. Cl. ...... 216/28; 216/96; 623/18.11; 623/23.55; 623/23.5

(58) Field of Classification Search .......... 148/525; 216/108, 109, 56, 83, 96; 424/422, 426; 427/2.26, 2.27; 433/201.1; 525/333.7; 606/60; 623/1.46, 18.11, 20.14, 23.5, 23.55, 23.6, 623/23.76
See application file for complete search history.

(56) References Cited

U.S. PATENT DOCUMENTS

| | | | | |
|---|---|---|---|---|
| 3,848,272 | A | * | 11/1974 | Noiles .................. 623/23.22 |
| 6,066,176 | A | * | 5/2000 | Oshida ................. 623/23.62 |
| 2004/0167633 | A1 | * | 8/2004 | Wen et al. ............. 623/23.57 |

FOREIGN PATENT DOCUMENTS
WO WO/92/05745 * 4/1992
* cited by examiner

*Primary Examiner* — Duy Deo
*Assistant Examiner* — Erin Flanagan

(57) ABSTRACT

The present invention relates to processes involving contacting articles that include titanium or titanium alloy with a solution comprising hydrochloric acid and chloride-containing compound for a time and at a temperature effective to form a plurality of indentions that, independently, have a diameter of from about 200 nm to 10 microns.

17 Claims, 14 Drawing Sheets

MICRO AND NANO SCALE SURFACE TEXTURED TITANIUM-CONTAINING ARTICLES AND METHODS OF PRODUCING SAME

CROSS REFERENCE TO RELATED APPLICATIONS

The present application claims benefit of U.S. Provisional Patent Application No. 61/169,443, filed Apr. 15, 2009, which is related to the following three applications, which are all filed on the same day: (i) U.S. Patent Application No. 61/169,365 entitled "Nanotextured Cobalt-Chromium Alloy Articles Having High Wettability and Method of Producing Same," having inventors Weidong Tong and Larry Salvati; (ii) U.S. patent application Ser. No. 12/424,000, entitled "Methods and Devices For Bone Attachment," having inventors Weidong Tong and Larry Salvati; and (iii) U.S. patent application Ser. No. 12/424,049, entitled "Methods and Devices for Implants With Calcium Phosphate," having inventors Weidong Tong, Larry Salvati and Pooja Kadambi. Each of the aforementioned applications are hereby incorporated herein by reference in their entirety.

TECHNICAL FIELD

The invention concerns, inter alia., nanotextured articles made from titanium or titanium alloy and methods for making and using same.

BACKGROUND

There are a number of design criteria which have long been sought for segmental bone replacement implants. These include that the implant should (1) last the lifetime of the patient without losing function or initiating any adverse process response; (2) restore the normal function of the bone in which it is implanted; and (3) be producible on a commercial scale. To satisfy the foregoing criteria, not only should the implant support the imposed load, often of a fluctuating nature, but the interface between the implant and the bone should also withstand the load requirement.

A plastic cement such as polymethyl methacrylate is often used to affix an implant to bone as well as to improve the fit between the implant and the bone. Implants also have been provided with porous coatings which mate with the bone and invite bone ingrowth such that, after a period of time, the prosthesis becomes integrated into the bone structure. Typical of such coatings are the those disclosed in U.S. Pat. Nos. 3,855,638; 4,206,516; 4,156,943; and 4,612,160.

Ceramic coatings have also been used to good effect and often are particularly desirable because of the affinity between bone and ceramic materials such as alumina ($Al_2O_3$). Typical of such coatings are those disclosed in U.S. Pat. Nos. 4,145,764 and 4,483,678 to which are particularly concerned with dental implants, and U.S. Pat. Nos. 4,309,488 and 4,846,837, which more broadly disclose implantable bone replacement material for use throughout the body.

An important method of promoting implant stability is osseointegration, i.e., forming a direct structural connection between living bone and the implant surface. It is generally known in the art that the osseointegration of metallic orthopaedic implants is dependent, in part, on the attachment and spreading of osteoblast-like cells on the surface of the orthopaedic implant. Studies suggest that such cells will more readily attach to rough or porous surfaces, as compared to smooth surfaces. As such, several attempts have been made to provide metallic orthopaedic implants having roughened and/or porous surfaces to aid in the osseointegration.

U.S. Pat. No. 5,236,459, for example, describes a process for forming an implant surface having "anchoring areas" in which a high-pressure liquid jet is used to remove a portion of the metal from the implant surface. The diameter of the "anchoring areas" can be varied from 0.5 to 1.5 mm.

U.S. Pat. No. 5,307,594 describes another method for forming a textured surface on orthopaedic implants. The method entails the application of a resilient mask, which contains several openings, to the surface of the implant and then subjecting the implant to high pressure blasting using a blasting media such as metal oxides particles. While this process can be used to produce implant surfaces having roughened surfaces, particles of the blasting media can become embedded in the surface of the implant. It is believed that these particles can negatively impact the osseointegration of the orthopaedic implant following implantation.

The methods described by the patents in the preceding paragraphs provide metallic implants having a roughened surface with surface features that are generally greater than 20 µm in size. While an orthopaedic implant having such surface features may exhibit improved osseointegration when compared to a smooth metallic implant, it is believed that osseointegration will be greatly improved if the implant surface includes smaller surface features (i.e., less than 20 µm in size).

Other work has utilized highly convoluted surfaces on the implant. U.S. Pat. Nos. 5,368,881 and 5,658,333 show use of non-spherical powder to produce a roughened surface for prosthesis. These surfaces, however, are known to have little to no inter-connected porosity.

In addition to the mechanical methods of providing a roughened surface described above, various chemical etching methods have been used to texture the surface of orthopaedic implants. U.S. Pat. No. 5,876,453, for example, describes a two-step process in which a hydrofluoric acid solution (10-50% HF) is used to remove the native oxide surface layer formed on the metallic implant, and a second acid treatment is used to further etch the metal to provide a roughened surface. The second acid treatment utilizes a mixture of two parts sulfuric acid (96% by weight $H_2SO_4$) and one part hydrochloric acid (37% by weight HCl). While this process and similar chemical etching processes are capable of producing roughened metallic implants having surface features at micron level, the process employs two very aggressive and highly concentrated acid solutions. One accordingly assumes a higher safety risk in storage and application than if less aggressive or low concentration acids are used.

Published U.S. Patent Application No. 2004/0167633 utilizes an etching solution comprising (i) at least one fluoride salt, (ii) at least one acid, and (iii) water for a time and under conditions sufficient to provide the implant with micron or nanometer-scale surface roughness.

Despite the progress made by the aforementioned art, there is a continued need for prosthesis surfaces with improved properties. In addition, there is a desire to avoid the use of high concentration acids such as HF or fluoride salts.

SUMMARY

The processes of the invention allow good surface roughening with small indentions without use of HF or acid solutions having fluoride salts. Thus, an advantage in safety and ease of manufacture is achieved. In certain embodiments, lower concentrations of acid can be utilized as compared with the state of the art. In addition, when used with orthopaedic implants, the small indentions produced by the processes described herein provide superior bone/implant bonding.

One aspect of the present invention concerns contacting an article that comprises at least one surface that includes titanium or titanium alloy with a solution comprising hydrogen ion ($H^+$) and chloride ion ($Cl^-$), in which the chloride ion is partially or completely attributed to the dissolution of the chloride containing salt, for a time and at a temperature effective to form a plurality of surface features that, independently, have a diameter of from about 200 nm to 10 microns. In some embodiments, the surface feature comprise a plurality of indentions that, independently, have a diameter of from about 200 nm to 10 microns. In certain preferred embodiments, $[Cl^-]/[H^+]$ is greater than 1. In some embodiments, the solution is substantially free of any oxidizing agent other than the chloride-containing compound.

In some processes, the solution has a hydrogen ion ($H^+$) concentration of at least about 0.07 N and a chloride ion ($Cl^-$) concentration of at least about 3 N. In addition, the solution further comprises a chloride-containing compound, other than HCl, producing a chloride ion concentration in the range of about 3 N to 8N. In some embodiments, the solution has a concentration of $H^+$ of about 0.07 to about 12 N and a concentration of $Cl^-$ that is greater than the concentration of $H^+$. Preferred chloride-containing compounds include sodium chloride (NaCl), potassium chloride (KCl), calcium chloride ($CaCl_2$), ammonium chloride ($NH_4Cl$), ferric chloride ($FeCl_3$), ferrous chloride ($FeCl_2$), cobalt chloride ($CoCl_2$), magnesium chloride ($MgCl_2$) and mixtures thereof.

In some embodiments, $H^+$ is derived from dissociation of acids of HCl, $HNO_3$, $H_3PO_4$, $H_2SO_4$, acetic acid, citric acid or combinations thereof.

In some process of the invention, the article is contacted with the solution at a temperature of about 20 to about 100° C., preferably about 20 to about 80° C. for certain processes. The article typically is contacted with the solution for about 30 minutes to about 24 hours, preferably 30 minutes to 5 hours in some embodiments.

Preferred surface compositions include, but are not limited to Ti6Al4V and commercially pure titanium. Some surfaces comprise titanium or titanium alloy beads or irregular shaped particles In certain embodiments, the process further comprises cleaning at least a portion of the surface and then drying the surface.

Some processes further comprise surface roughening before contacing the surface with the etching solution. The surface roughening includes, but is not limited to, grit-blasting, high pressure water jet cleaning, mechanical rubbing with sand paper. In some embodiments, the grit-blasting media includes, but not limited to, alumina, silica, zirconia, stainless steel, titanium, calcium phosphate or combinations Certain articles produced in accordance with the present invention are generally suitable for implantation into a mammal such as a human. Some articles are a joint replacement prosthesis or component thereof. Certain articles are a hip or knee replacement prosthesis.

DETAILED DESCRIPTION OF ILLUSTRATIVE EMBODIMENTS

Figure 1A:
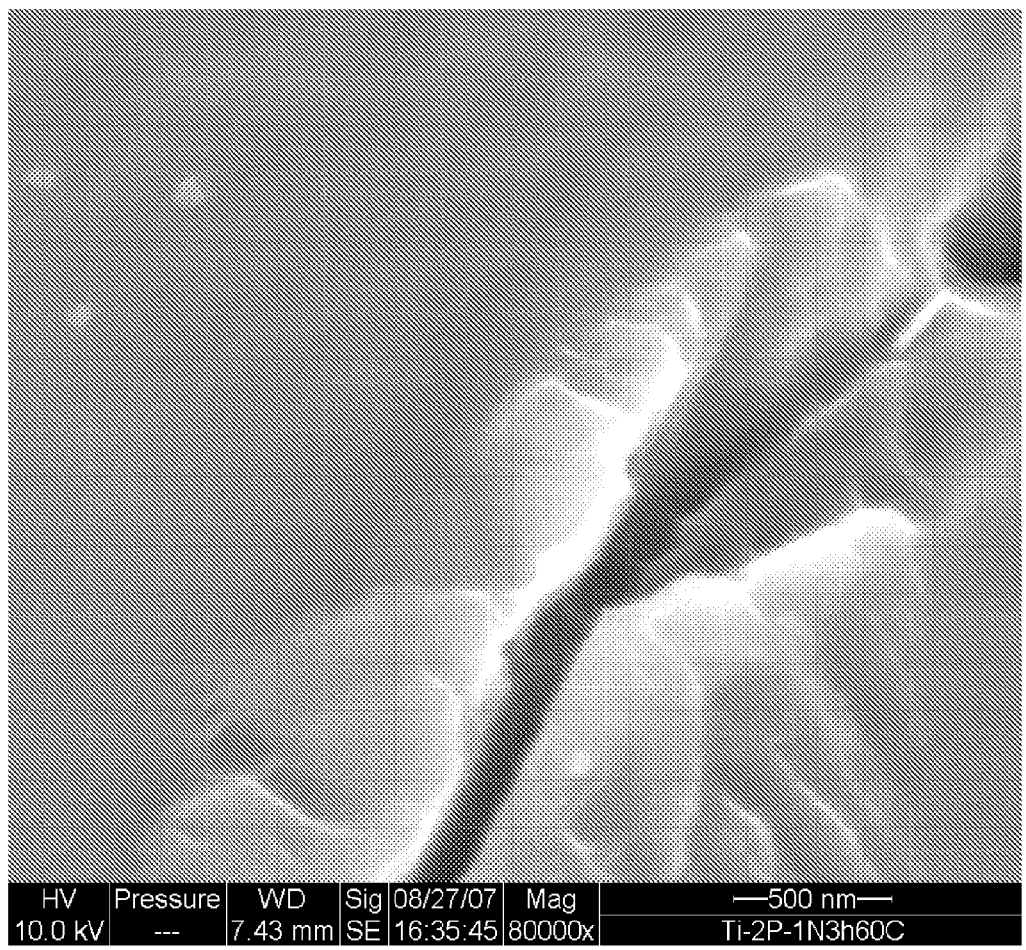
FIG. 1 shows micrographs of Ti Porocoat® beads exposed to 1N HCl for 3 hour at 60° C.

The materials and articles of the present invention have at least one surface that comprises either titanium or a titanium alloy. One form of suitable titanium is commercially pure titanium. One suitable titanium alloy useful in implants contains 6% aluminum and 4% vanadium by weight. This alloy is commonly referred to as Ti6Al4V. Suitable surfaces include Porocoat® Porous Coatings (found on certain implants marketed by DePuy Orthopaedics, Inc.) which employ a three-dimensional beaded coating that allows tissue ingrowth and can eliminate the need for bone cement. Additional suitable surfaces include Ti Gription® porous coating (found on certain implants marketed by DePuy Orthopaedics, Inc.) which employs Ti irregular particles over beaded Ti.

In certain etching solutions of the invention, the concentration of protons is at least 0.8 N and the concentration of chloride is at least about 1N. In other processes, the solution has a concentration of $H^+$ of at least about 0.07 N and a concentration of $Cl^-$ is at least 6N. In some processes, the solution has a concentration of $H^+$ of at least about 0.07 N and a concentration of $Cl^-$ is greater than the concentration of H. The solution can further comprise a chloride-containing compound at a concentration in the range of about 0.01 N to 10 N. In some embodiments, the solution has a concentration of $H^+$ of about 0.07 to about 12N and a concentration of $Cl^-$ that is greater than the concentration of H. Preferred chloride-containing compounds include sodium chloride (NaCl), potassium chloride (KCl), calcium chloride ($CaCl_2$), ammonium chloride ($NH_4Cl$), ferric chloride ($FeCl_3$), ferrous chloride ($FeCl_2$), cobalt chloride ($CoCl_2$), magnesium chloride ($MgCl_2$) and mixtures thereof.

In some embodiments, $H^+$ is derived from dissociation of acids of HCl, $HNO_3$, $H_3PO_4$, $H_2SO_4$, acetic acid, citric acid or combinations thereof.

The article can be contacted with the solution at any temperature suitable for modifying the surface. In some embodiments, the article is contacted with the solution at a temperature of about 20 to about 100° C., or in some embodiments, at a temperature of about 20 to about 80° C. The article can be contacted with the solution for a time sufficient to provide the desired surface properties. In some processes, for example, the article is contacted with the solution for about 30 minutes to about 24 hours. In other processes, the article is contacted with the solution for about 1 to about 24 hours or about 30 minutes to about 5 hours.

At various points in the processes of the instant invention, the substrate surface can optionally be cleaned using typical usual cleaning procedures, such as degreasing with detergent or an alkaline solution. Ultrasonic cleaning in detergent, followed by ultrasonic cleaning in water and drying, may degrease the substrate surface. In some embodiments, the entire implant is cleaned. In other embodiments, only a portion of the implant will be cleaned. One skilled in the art will readily appreciate that there may be a desire to perform an initial cleaning step before treating the surface with the processes disclosed herein. It may be desired to clean the surface between steps of the processes and/or at the end of the processes disclosed herein. Some cleaning steps might involve rinsing with soaking in water and followed by drying the surface.

The articles of the present invention can also be dried after the aforementioned cleanings Application of heat and/or vacuum to the article can be used to facilitate the removal of water.

It has been found that using aqueous HCl solutions of the instant invention which contain at least one additional chloride-containing compound, have superior etch power to solutions that do not contain the additional chloride-containing compound.

In some embodiments, the surface features are depressions, indentions, divots or craters in the titanium surface. Some surface features, independently, have a diameter of from about 200 nm to 10 microns.

The articles described herein are suitable for implantation into a mammal. Certain of these articles are prosthesis devices, such as a joint replacement prosthesis or component thereof. These devices include hip or knee replacement prosthesis.

The invention also concerns implanting the articles described herein into a mammal. In some embodiments, the articles are suitable for implant in humans.

In some embodiments, an implant or component thereof can be manufactured by conventional means to have a titanium or titanium alloy surface. This implant or component can be treated by methods described herein to produce an implant or component having a nanotextured surface.

The invention is illustrated by the following examples that are intended to be illustrative and not limiting.

EXAMPLES

Acid solutions: Chloride containing salts can be added into acid to increase the chloride concentration. Various amounts of NaCl, $NH_4Cl$ and $CaCl_2.2H_2O$ were added in 100 ml 4N HCl at room condition with stirring (Table 1). Final volume was measured and used to calculate the ion concentrations. $[H^+]$, $[Cl^-]$ and metal ion concentrations ($[M]$) are listed in table 1. Maximum $[Cl^-]$ is reached by using $CaCl_2.2H_2O$.

TABLE 1

| Chemical | Final concentration (N) | | |
|---|---|---|---|
| | $[H^+]$ | $[Cl^-]$ | $[M]^*$ |
| NaCl | 3.5 | 5.3 | 5.3 |
| $NH_4Cl$ | 2.7 | 5.4 | 5.4 |
| $CaCl_2 \cdot 2H_2O$ | 3.3 | 7.9 | 2.3 |

$[M]^*$ can be $Na^+$, $NH_4^+$ or $Ca^{2+}$

In the examples listed in Table 2, calcium chloride was dissolved in 100 ml of water (RO), 0.1N HCl, 1N HCl, 3N HCl and 6N HCl, separately. Volume was measured after complete dissolution of calcium chloride in the aqueous solution (final volume usually exceeds starting volume). Ion concentrations are calculated according to the final volume. pH of the solution was measured before and after adding calcium chloride (781 pH/Ion Meter, Metrohm; pH probe, Metrohm, 6.0258.010 pH0-14, 0-100° C., Pt1000/B/2/3MKCl, pH probe calibrated using pH standards 4 and 7). pH usually drops after adding calcium chloride. In certain occasions, negative readings were observed (negative readings of pH is usually observed for HCl acid stronger than 1N, the higher the HCl acid concentration, the more negative the pH readings).

TABLE 2

| HCl | $CaCl_2$— | Final concentration (N) | | | pH | |
|---|---|---|---|---|---|---|
| CONC N | Vol ml | 2H2O G | [H] N | [Cl] N | [Ca] N | Before adding | After adding |
| 0 | 100 | 78 | 0.00 | 7.92 | 3.96 | 5.65 | 2.70 |
| 0.1 | 100 | 78 | 0.07 | 7.99 | 3.96 | 1.01 | −0.72 |
| 1 | 100 | 70 | 0.83 | 8.77 | 3.97 | 0.00 | −1.25 |
| 3 | 100 | 40 | 2.56 | 7.22 | 2.33 | n/a | n/a |
| 6 | 100 | 37 | 5.00 | 9.20 | 2.10 | n/a | n/a | n/a = not available

Calcium chloride supplemented 1N HCl is prepared by adding 70 g of $CaCl_2.2H_2O$ powder in 100 ml of 1N HCl with stirring. The dissolution process is exothermic and the dissolution can be enhanced by cooling water bath. Volume is measured after the calcium chloride is fully dissolved (no visible particles on the bottom of the container after settle for more than 5 minutes). The final concentrations in the chloride supplemented HCl acid are approximately $[H^+]$=0.8 N, $[Cl^-]$=8.8 N, $[Ca^{2+}]$=4 N.

Ultrasound cleaning: after completing each acid soaking time, each of the test sample was rinsed in RO water and followed ultraound cleaning in RO for 20 minutes, 10 minutes and 5 minutes. The samples were then blow dried with nitrogen and thermally dried at 60° C. oven for at least 2 hours.

Etching process: The flat disks used for the etching experiments were made of Ti6Al4V with one mirror polished surface. The porous coated disks used for the etch experiments were constructed of Ti6Al4V and had a porous surface by sintering Ti beads or irregular shaped Ti particles over the Ti6Al4V metal substrate. The size of the beads or particles may range from 50 microns to 400 microns. During etch process, only the mirror polished Ti6Al4V surface or the porous coated surface were exposed to the acid. Each test disk (flat or porous coated) was either soaked in 50 ml acid (1N HCl or 1N HCl supplemented with calcium chloride) and immediately stored in oven at 60° C. for 1 hr to 6 hrs or they were soaked in an pre-heated acid (pre-heated at 60° C. for 30 minutes) and immediately stored in oven at 60° C. for 1 hr to 6 hrs. In all etch processes, the containers were tightly sealed.

The invention is illustrated by the following examples that are intended to be illustrative and not limiting.

Example 1

Etched Ti6Al4V flat disks, as described above, were soaked in 1 N HCl aqueous solution (without chloride supplement) and immediately stored in a 60° C. oven for 1 hour and 3 hours, respectively. Additional etched flat disks were soaked in a 1N HCl supplemented with calcium chloride ($[H^+]$=0.8 N, $[Cl^-]$=8.8 N, $[Ca^{2+}]$=4 N) and immediately stored in a 60° C. oven for 1 hour and 3 hours, respectively. The etch power was measured and reported in Table 3. Etch power (EP) is equal to the weight loss per unit surface area. For flat disks without porous coating, EP is equal to the weight loss divided by the surface area. Weight loss is determined by the weight change before and after etch process.

Surface area is equal to $\pi D^2/4$, where D is the diameter of the metal disk. For a 1" flat disk, the surface area is 0.79 in$^2$. For a porous coated disk, the projected surface area is used which is equal to $\pi D^2/4$ (D is the diameter of the metal substrate)

Table 3 lists the EP of mirror polished Ti6Al4V disks (Ra=0.05±0.01µ). After 1 hr etch, there is no measurable weight change; at 3 hr, the calcium chloride supplemented group shows 6-fold increase of EP (Ra=0.16±0.02µ).

TABLE 3

| | Etch Power (mg/in$^2$) n = 2 | |
|---|---|---|
| | 1 N HCl | 1N HCl supplemented with Chloride |
| Ti6Al4V - 1 hr | 0.0 +/− 0.0 | 0.0 +/− 0.1 |
| Ti6Al4V - 3 hr | 1.5 +/− 0.3 | 9.9 +/− 1.1 |

Example 2

Figure 1B:
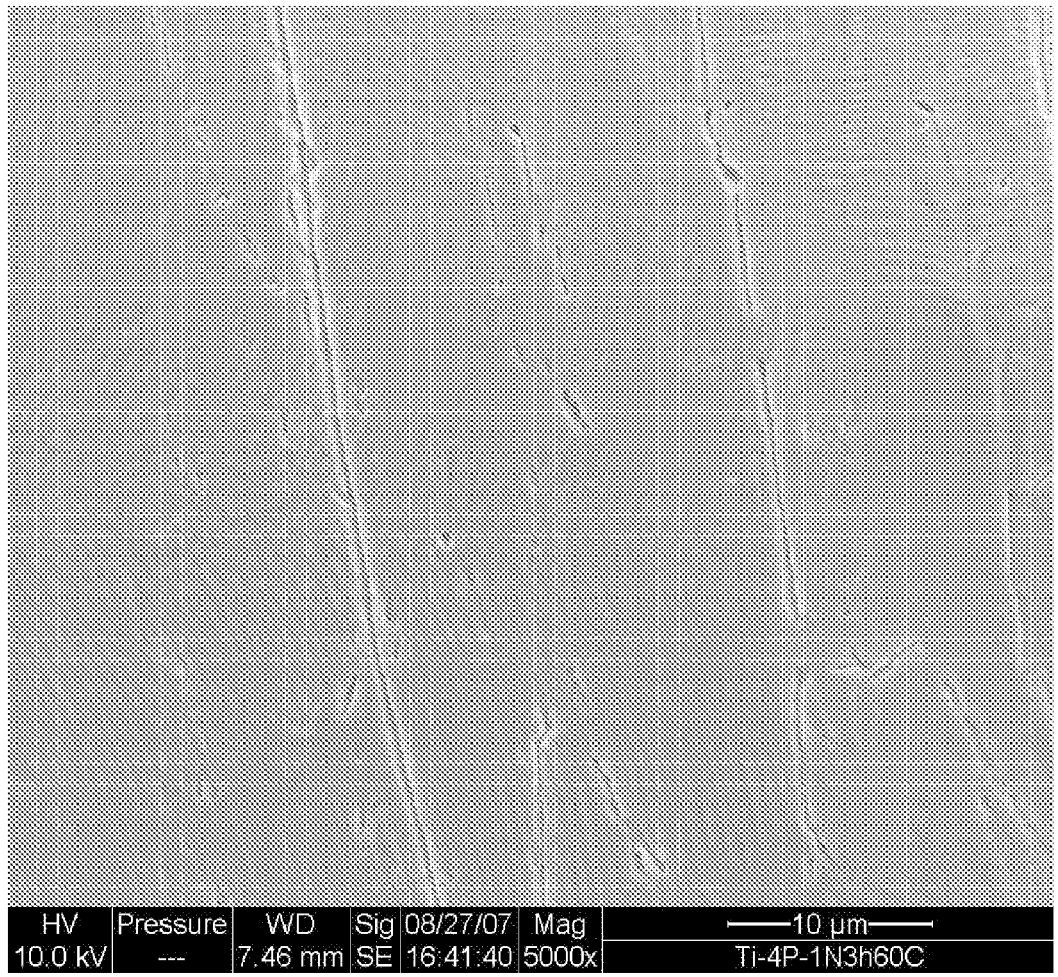
Figure 1C:
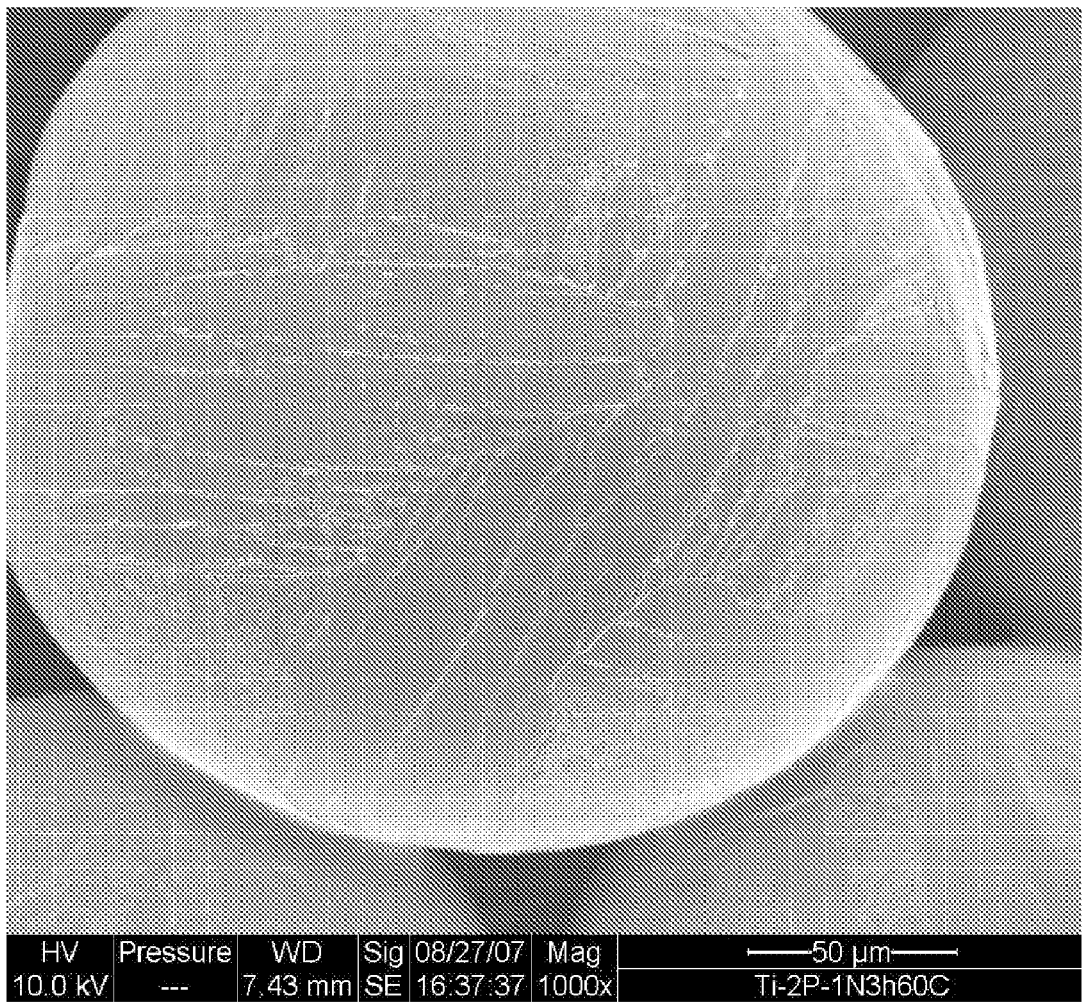
Figure 2A:
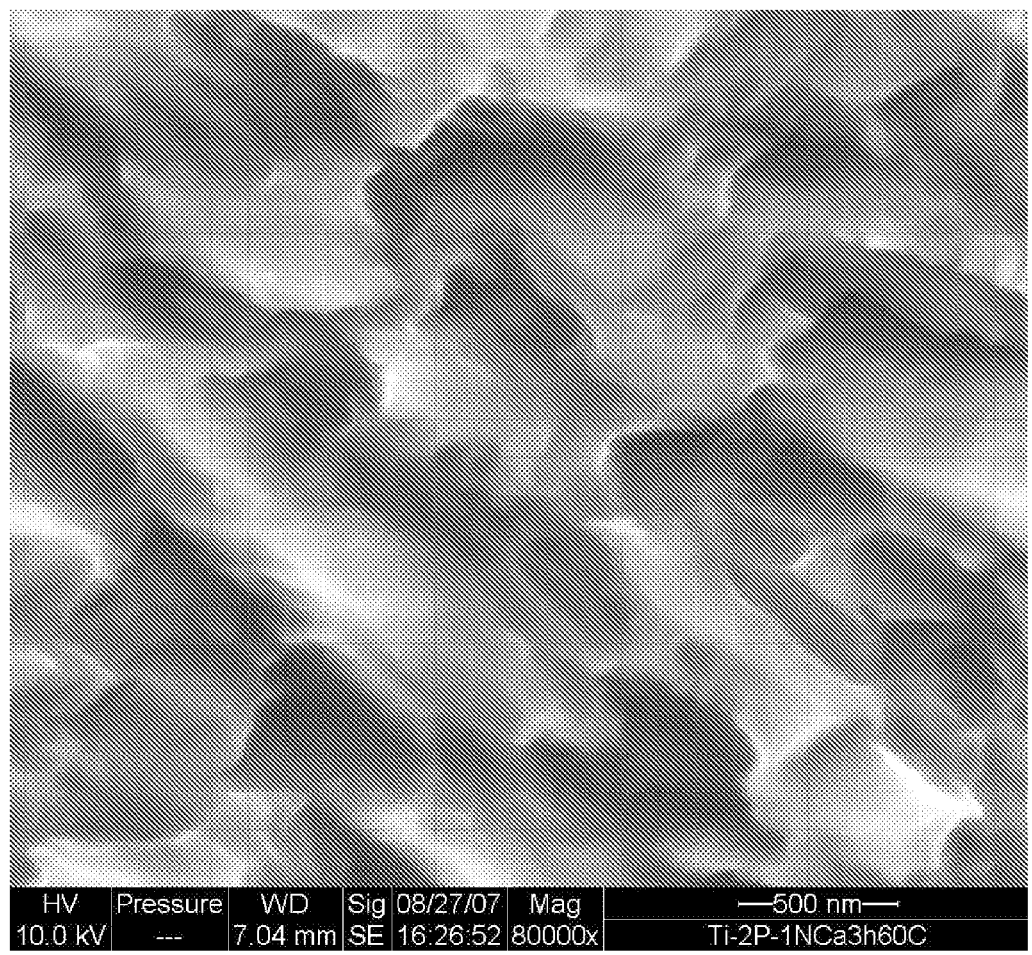
FIG. 2 shows micrographs of Ti Porocoat® beads exposed to 1N HCl and $CaCl_2$ supplement for 3 hours at 60° C.
Figure 2B:
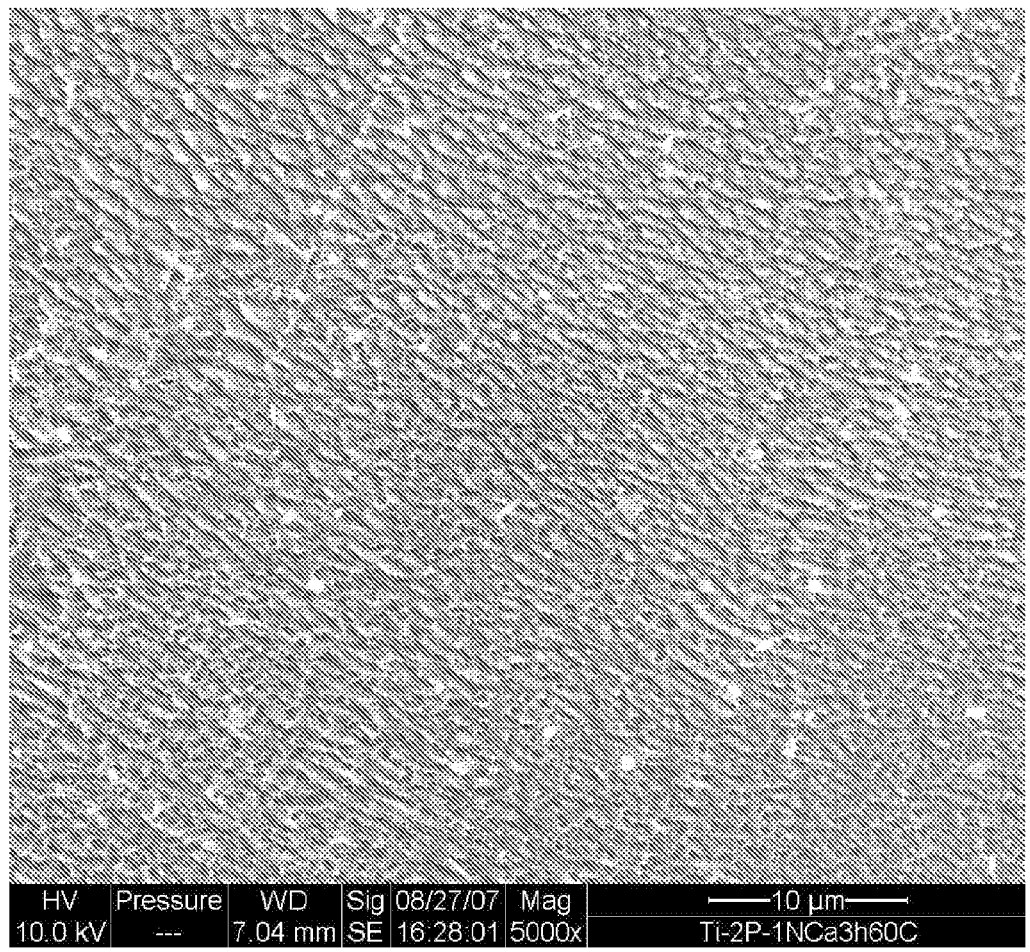
Figure 2C:
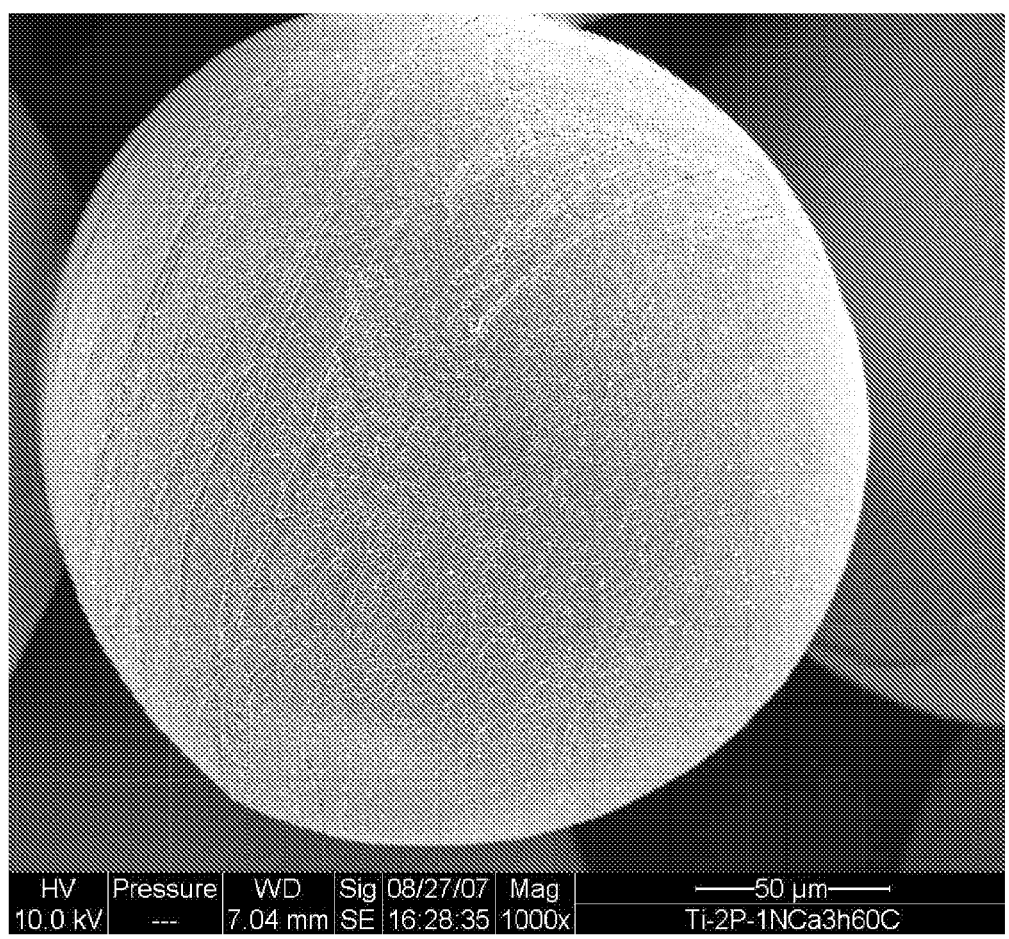

Etched Ti6Al4V Porocoat® disks, as described above were soaked in 1 N HCl aqueous solution (without chloride supplement) and immediately stored in a 60° C. oven for 1 hour and 3 hours, respectively. Additional Ti6Al4V Porocoat® disks were soaked in a 1N HCl supplemented with calcium chloride ([H$^+$]=0.8 N, [Cl$^-$]=8.8 N, [Ca$^{2+}$]=4 N) and immediately stored in a 60° C. oven for 1 hour and 3 hours, respectively. FIG. 1A-C shows the SEM images of the Porocoat® treated 1N HCl only; FIG. 2A-C shows the SEM images of the Porocoat® treated with 1N HCl supplemented with calcium chloride.

Example 3

Figure 3A:
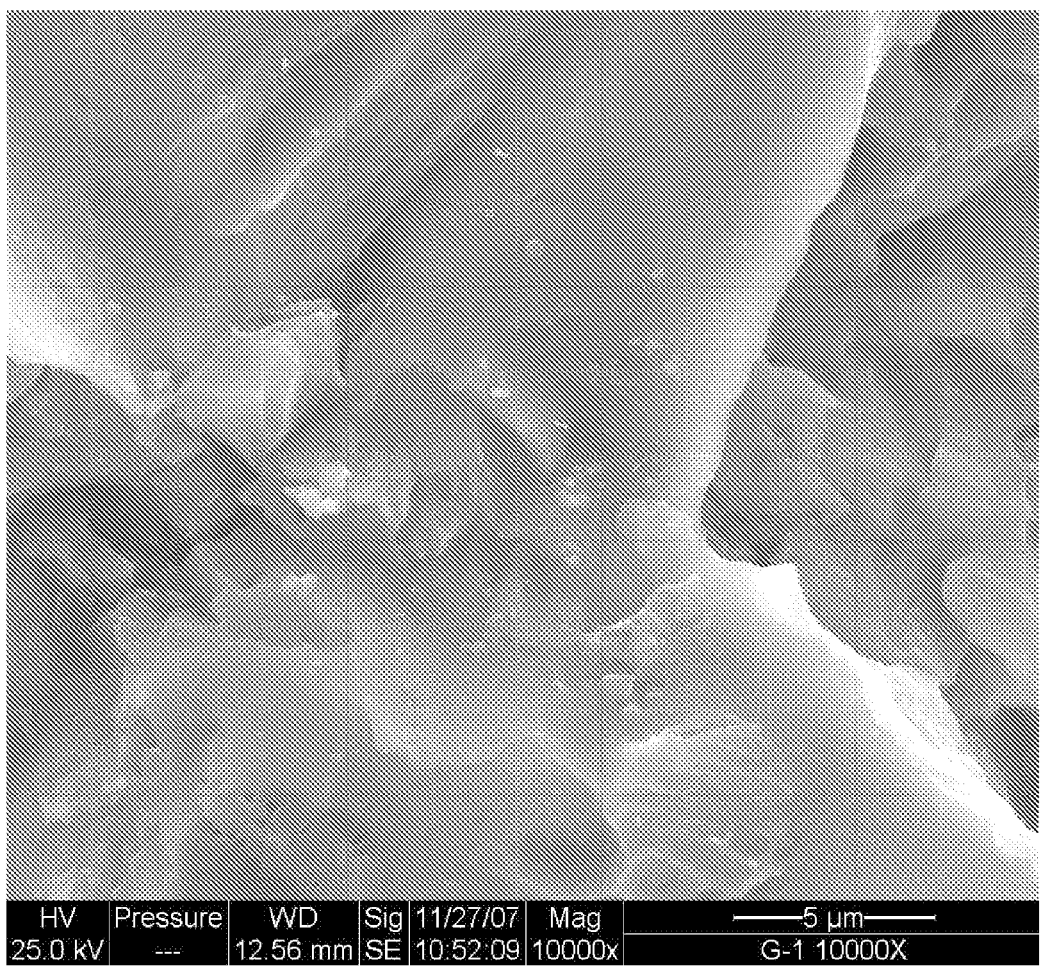
FIG. 3 shows micrographs of 20 grit alumina grit-blasted Ti6Al4V surface (FIG. 3A) and that exposed to 1N HCl supplemented with calcium chloide for 3 hours at 60° C.
(FIG. 3B)
Figure 3B:
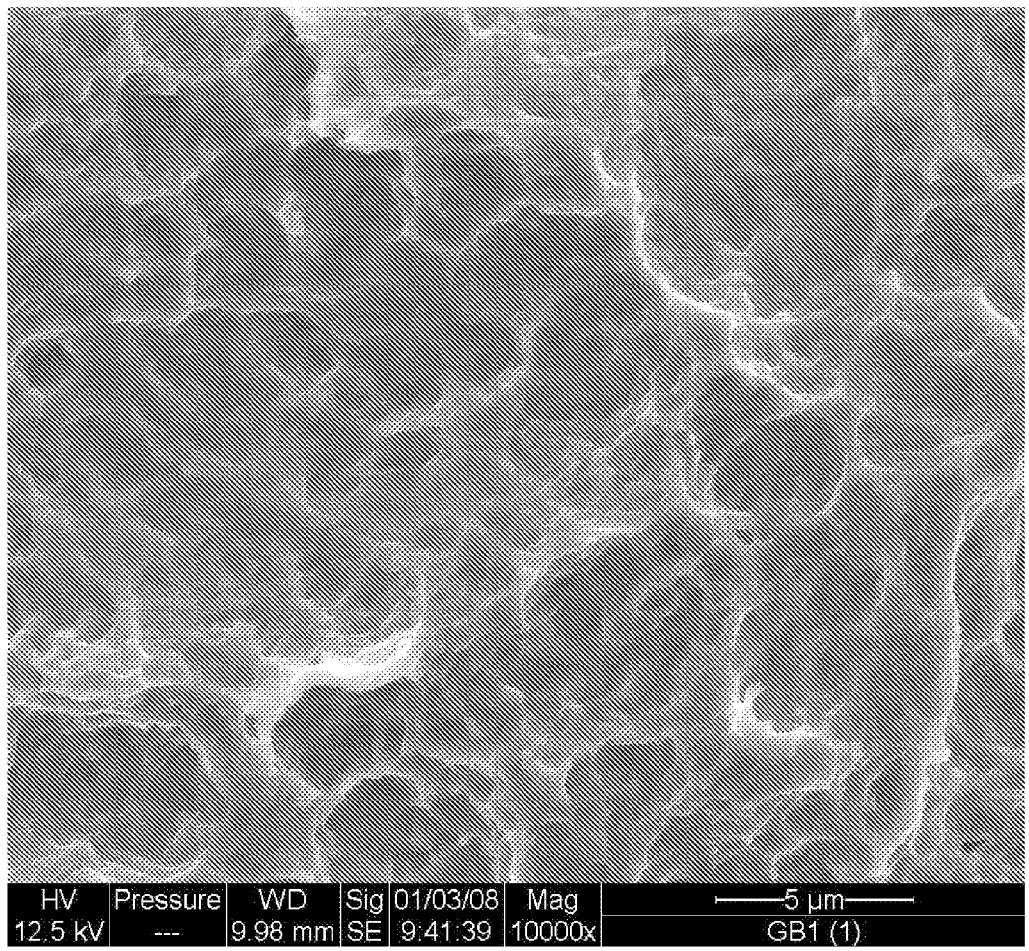

Table 4 presents analysis of 20 grit blasted (GB) Ti6Al4V surface (Ra=3.5 to 6 micron) that was etched with 1N HCl supplemented with calcium chloride ([H$^+$]=0.8 N, [Cl$^-$]=8.8 N, [Ca$^{2+}$]=4 N). See, FIG. 3. The results from surface analysis by X-ray photoelectron spectroscopy (XPS) are shown in Table 4. To verify surface chemistry, X-ray photoelectron spectroscopy (Quantera, Physical Electronics PHI, Eden Prairie, Minn.) was used. Disks were placed on a specially designed aluminum platen in a vacuum chamber. Three 200 µm×200 µm surface areas were analyzed. High-powered surface survey scans were collected along with high-resolution atomic concentration of designated elements. XPS high-resolution parameters are detailed here. Five elements were examined (C1s, O1s, Al2p, Ti2p and V2p3) at Pass Energy of 55.00 EV. The GB Ti6Al4V surface has an exceedingly high Al/Ti equal to 3.2 (atomic ratio) due to the embedded surface contamination by grit-blasting medium. The etched GB Ti surface has a ten-fold reduction of the Al/Ti ratio due to the removal of the grit-blasting medium on the surface.

TABLE 4

| | C1s | O1s | Al2p | Ti2p | V2p3 | Al:Ti |
|---|---|---|---|---|---|---|
| Titanium GB Control | 16.8 | 59.1 | 18.4 | 5.8 | 0.0 | 3.2 |
| Titanium GB Etch | 33.3 | 50.1 | 4.0 | 12.6 | 0.0 | 0.3 |
| Titanium Polished Control | 28.0 | 52.8 | 3.2 | 16.0 | 0.0 | 0.2 |

Example 4

Figure 4:
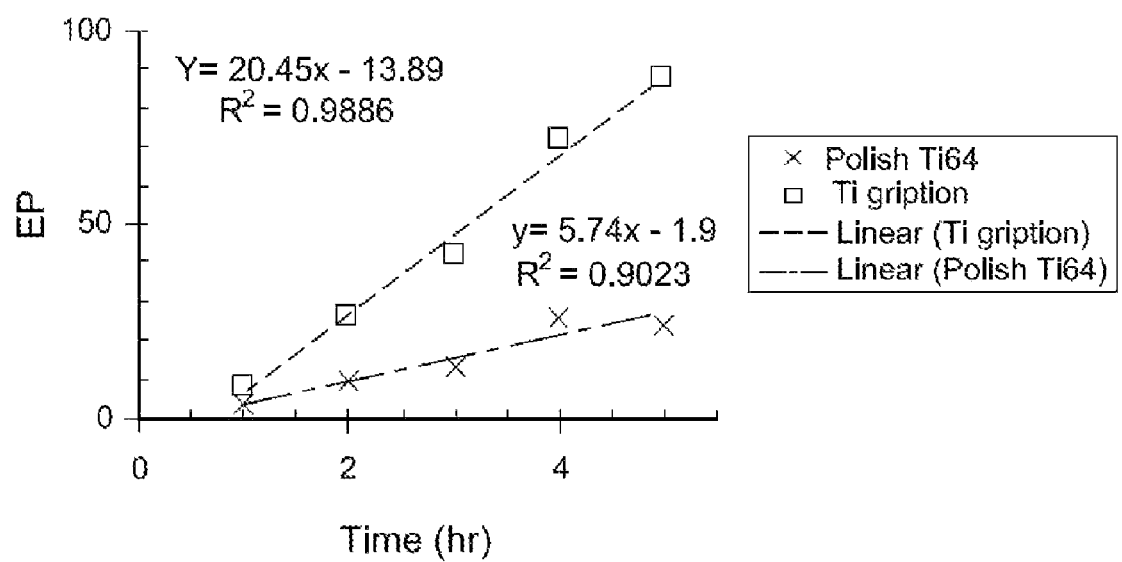
FIG. 4 shows etch power (EP) vs. time for both polished Ti6Al4V disks and Ti Gription® coated disks.
Figure 5A:
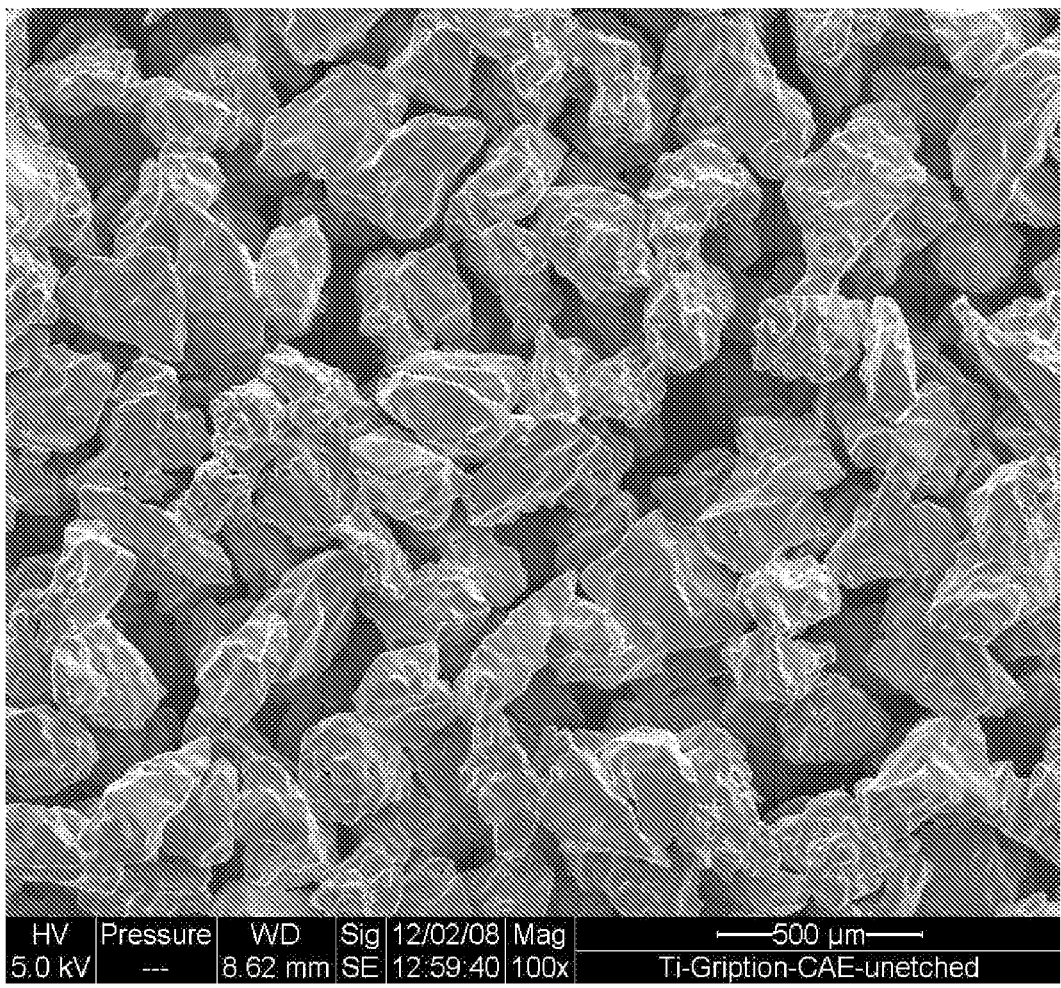
FIG. 5 shows SEM images of Ti Gription® coating after soaked in the etch solution for 4 hrs. (A&B) unetched Ti Gription®. Note the smooth area and the step-like feature; (C&D) Ti Gription® after 4 hr soaking in 1N HCl supplemented with calcium chloride. Note evenly distributed etched irregular pits.
Figure 5B:
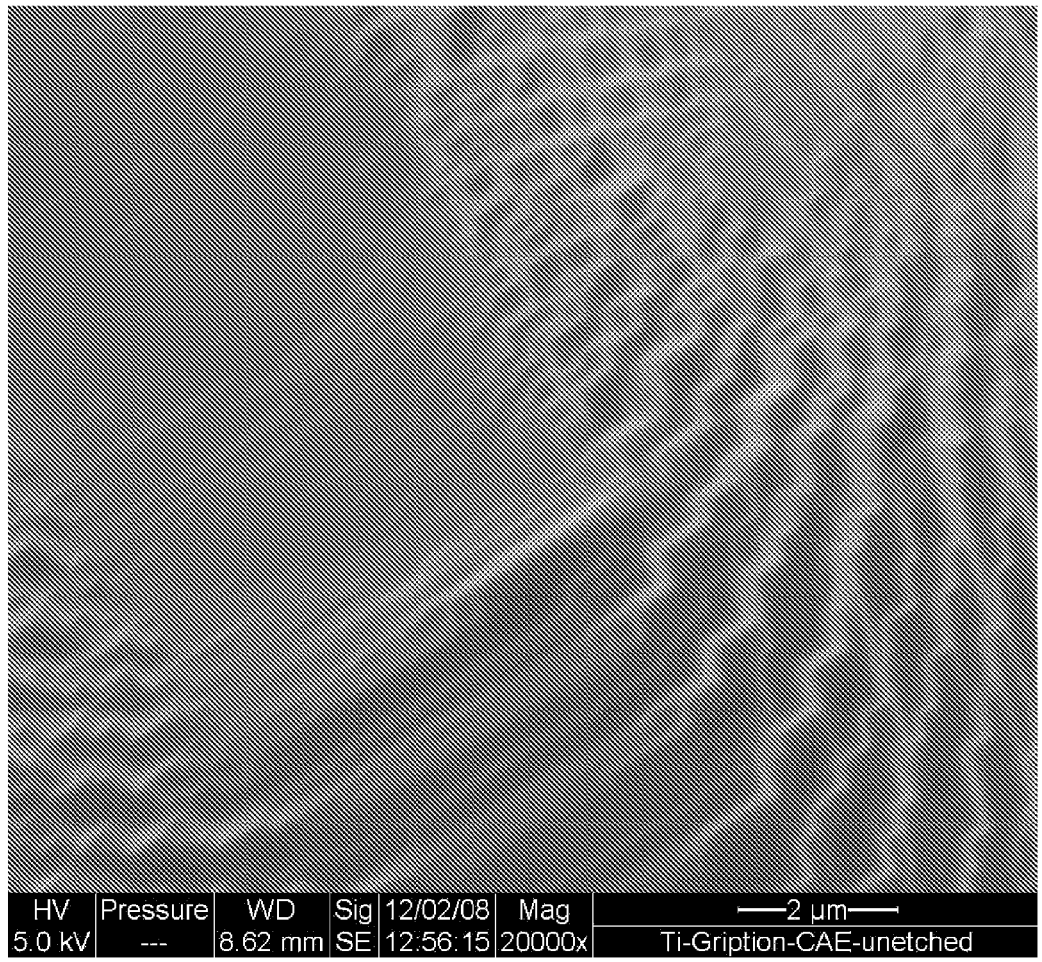
Figure 5C:
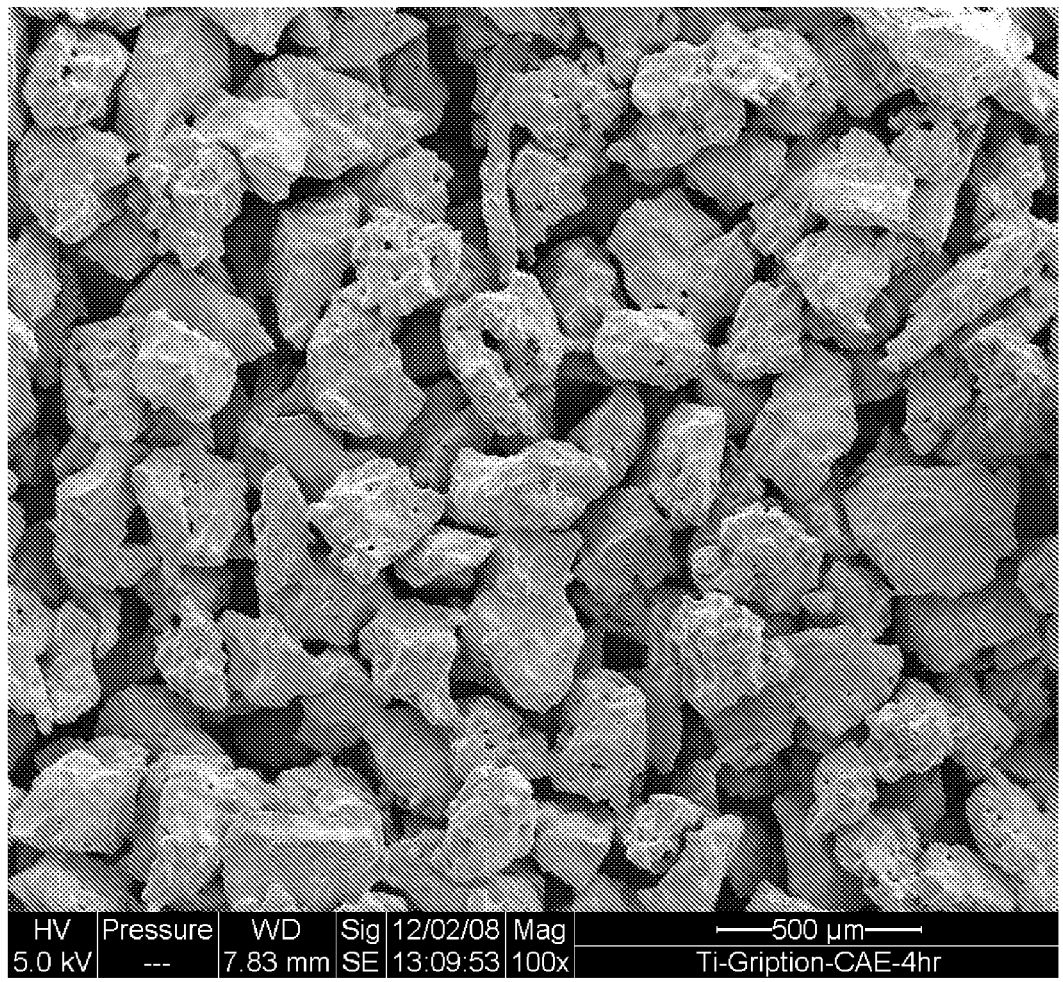
Figure 5D:
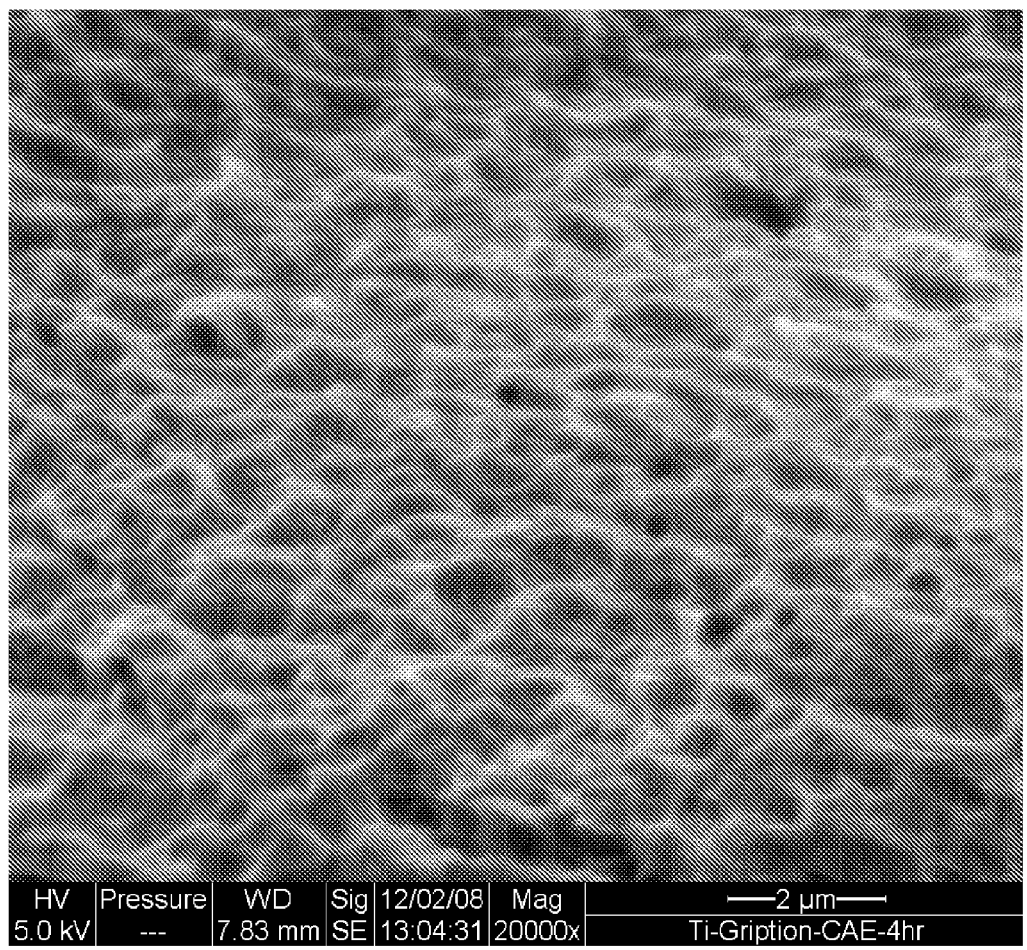

Five Ti Gription® disks and five polished Ti6Al4V disks were tested, each soaked in 50 ml 1N HCl supplemented with calcium chloride. The etch solution was pre-heated in an oven (60° C.) for 30 minutes. Each test disk was soaked in 50 ml etch solution at 60° C. for 1 hr to 6 hrs. FIG. 4 shows EP vs. time for both polished disks and Ti Gription® coated disks. FIG. 5 shows SEM images of Ti Gription coating after soaked in the etch solution for 4 hrs.

Example 5

Figure 6:
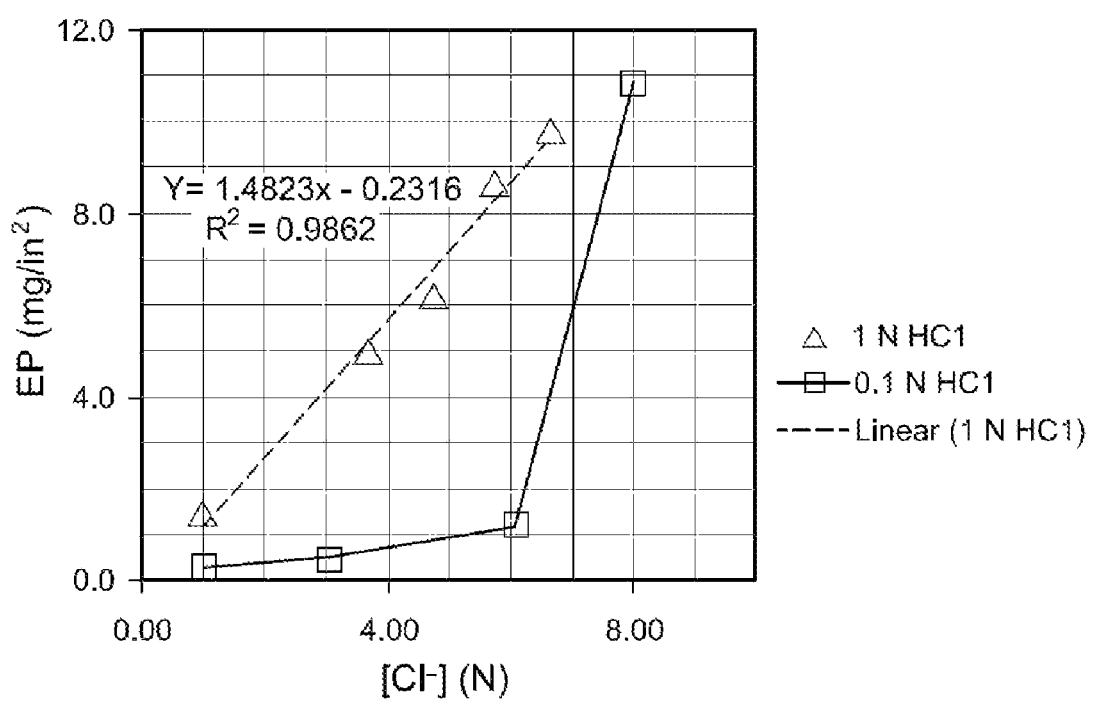
FIG. 6 shows the dependence of etch power vs. chloride ion concentration in the etch solution. Etch solution was prepared by adding calcium chloride dihydrate in 1N HCl and 0.1N HCl, respectively.

Varying amount of calcium chloride dihydrate was added into 100 ml of dilute HCl acids ranging from 0.0001 to 1N. Final concentrations of hydrogen ion and chloride ion are calculated based on the final volume (Table 5). Each 1" polished Ti6Al4V disk was immersed in 50 ml of supplemented solution and treated for 3 hrs at 60° C. Weight change was measured before and after treatment. As HCl acid <0.01, EP=0 regardless of [Cl$^-$]. As HCl=0.1 N, EP shows dramatic increase at [Cl$^-$] higher than 6N; As HCl=1N, EP shows roughly linear dependence on [Cl$^-$] (FIG. 6).

TABLE 5

| HCl | | CaCl$_2$— | Final concentration (N) | | | pH | | EP | | |
|---|---|---|---|---|---|---|---|---|---|---|
| CONC | Vol | 2H$_2$O | [H] | [Cl] | [Ca] | acid | acid + CaCl$_2$ | Mean | std | |
| N | ml | g | N | N | N | | | mg/in$^2$ | mg/in$^2$ | n= |
| 0.0001 | 100.0 | 78.00 | 0.0001 | 7.92 | 3.96 | 3.98 | 3.46 | 0.2 | 0.0 | 2 |
| 0.0010 | 100.0 | 78.00 | 0.0007 | 7.92 | 3.96 | 3.00 | 1.50 | 0.2 | 0.1 | 2 |
| 0.0100 | 100.0 | 78.00 | 0.0074 | 7.90 | 3.95 | 2.02 | −0.10 | 0.1 | 0.2 | 2 |
| 0.1000 | 100.0 | 78.00 | 0.0746 | 7.99 | 3.96 | 1.00 | −1.10 | 10.9 | 0.8 | 2 |
| 0.1000 | 100.0 | 54.00 | 0.0816 | 6.08 | 3.00 | 1.02 | −0.34 | 1.2 | 0.4 | 2 |
| 0.1000 | 100.0 | 24.00 | 0.0917 | 3.09 | 1.50 | 1.02 | 0.35 | 0.5 | 0.2 | 2 |
| 0.1000 | 100.0 | 7.00 | 0.0985 | 1.04 | 0.47 | 1.02 | N/A | 0.3 | 0.0 | 2 |
| 1.0000 | 100.0 | 52.00 | 0.8230 | 6.65 | 2.91 | 0.00 | −0.73 | 9.8 | 0.0 | 2 |
| 1.0000 | 100.0 | 42.00 | 0.8547 | 5.74 | 2.44 | 0.00 | −0.59 | 8.7 | 0.7 | 2 |
| 1.0000 | 100.0 | 32.00 | 0.8850 | 4.74 | 1.93 | 0.00 | −0.45 | 6.2 | 0.1 | 2 |
| 1.0000 | 100.0 | 22.00 | 0.9217 | 3.68 | 1.38 | 0.00 | −0.29 | 5.0 | 0.8 | 2 |
| 1.0000 | 100.0 | 0.00 | 1.0000 | 1.00 | 0.00 | 0.00 | 0.00 | 1.5 | 0.3 | 2 |

EP: etch power; std: standard deviation

What is claimed:

1. A process comprising contacting an article that comprises at least one surface that includes titanium or titanium alloy with a solution comprising hydrogen ion (H$^+$) in a concentration of at least about 0.07N and chloride ion (Cl$^-$) in a concentration of at least about 3N, in which the chloride ion is partially or completely attributed to the dissolution of at least one chloride containing salt and without the use of HF or fluoride salts, for a time and at a temperature effective to form a plurality of surface features that, independently, have a diameter of from about 200 nm to 10 microns.

2. The process of claim 1, wherein said solution has a concentration of $H^+$ ranging from about 0.07 N to about 12N and a concentration of $Cl^-$ ranging from about 3N to about 8N.

3. The process of claim 1, wherein said solution has a concentration of concentration of $H^+$ about 0.07 N and the concentration of $Cl^-$ is at least 6N.

4. The process of claim 2, wherein said chloride-containing compound is sodium chloride, potassium chloride, calcium chloride, ammonium chloride, ferric chloride, ferrous chloride, cobalt chloride, magnesium chloride or mixtures thereof.

5. The process of claim 2, wherein said $H^+$ derives from dissociation of acids of HCl, $HNO_3$, $H_3PO_4$, $H_2SO_4$, acetic acid, citric acid or combinations thereof.

6. The process of claim 1, wherein the article is contacted with the solution at a temperature of about 20 to about 100° C.

7. The process of claim 1, wherein the article is contacted with the solution for about 30 minutes to 5 hrs.

8. The process of claim 1, wherein said surface comprises titanium or titanium alloy beads.

9. The process of claim 1, wherein said surface comprises Ti6Al4V.

10. The process of claim 1, wherein said surface comprises commercially pure titanium.

11. The process of claim 1, further comprising surface roughening before contacting with the said solution.

12. The process of claim 11, wherein said surface roughening is accomplished by grit-blasting, high pressure water jet cleaning, or mechanical rubbing with sand paper.

13. The process of claim 12, wherein grit-blasting comprises at least one of alumina, silica, zirconia, stainless steel, titanium oxide, calcium phosphate or combinations.

14. The process of claim 1, wherein said article is a joint replacement prosthesis or component thereof.

15. The process of claim 14, where said article is a hip or knee replacement prosthesis.

16. The process of claim 2, wherein said chloride-containing compound is calcium chloride and the $H^+$ is derived from dissociation of HCl.

17. A process comprising contacting an article that comprises at least one surface that includes titanium or titanium alloy with a HCl solution comprising hydrogen ion ($H^+$) in a concentration of at least about 0.07N and chloride ion ($Cl^-$) in a concentration of at least about 6N, in which the chloride ion is partially attributed to the dissolution of calcium chloride and without the use of HF or fluoride salts, for a time and at a temperature effective to form a plurality of surface features that, independently, have a diameter of from about 200 nm to 10 microns.

* * * * *